United States Patent [19]
Britton et al.

[11] Patent Number: 5,650,192
[45] Date of Patent: Jul. 22, 1997

[54] METHOD FOR MANUFACTURING BUCCAL DELIVERY DEVICE

[76] Inventors: Peter Britton, 1133 S. Martine Ave., Scotch Plains, N.J. 07076; Patricia Flanagan, 765 S. River Rd., Naperville, Ill. 60540; William P. Hart, 47 Wellington Rd., Freehold, N.J. 07728; Deborah Linkin, 315E Medallion Blvd., Maderia Beach, Fla. 33708

[21] Appl. No.: 500,007

[22] Filed: Jul. 10, 1995

Related U.S. Application Data

[60] Division of Ser. No. 104,785, Aug. 16, 1993, Pat. No. 5,458,884, which is a continuation-in-part of Ser. No. 943,360, Sep. 10, 1992, abandoned.

[51] Int. Cl.$^6$ ................... A61J 3/00; A61K 9/19
[52] U.S. Cl. .............. 427/2.19; 34/284; 34/287; 261/DIG. 26; 424/430; 424/433; 424/434; 424/435; 514/182; 514/945; 514/965
[58] Field of Search ................ 427/2.19, 2.21, 427/213.31, 213.36; 424/430, 434, 435, 494, 433; 514/945, 963, 182; 34/287, 284; 264/4.6

[56] References Cited

U.S. PATENT DOCUMENTS

| | | | |
|---|---|---|---|
| 3,309,779 | 3/1967 | Ginnette et al. | 34/287 |
| 3,939,260 | 2/1976 | Lafon | 424/435 X |
| 4,642,903 | 2/1987 | Davies | 34/284 |
| 4,948,580 | 8/1990 | Browning | 424/434 |
| 5,354,558 | 10/1994 | Britton et al. | 424/433 |
| 5,458,884 | 10/1995 | Britton et al. | 424/435 |

*Primary Examiner*—Richard D. Lovering

[57] ABSTRACT

The invention relates to a muco-adherent, soluble device for administering active ingredients, a method of using said device, and an improved method of manufacturing said device using a continuous, enclosed mixing device capable of operating under pressure. The devices of the invention, which comprise a lyophilized foam and an active ingredient, have a dissolution time of at least about 8 hours, and preferably at least about 24 hours, and can provide for the sustained and/or controlled release of an active ingredient for up to about 24 hours.

9 Claims, No Drawings

METHOD FOR MANUFACTURING BUCCAL DELIVERY DEVICE

REFERENCE TO RELATED APPLICATION

This is a division of application Ser. No. 08/104,785, filed Aug. 16, 1993, now U.S. Pat. No. 5,458,884, which is a continuation-in-part of application Ser. No. 07/943,360, filed Sep. 10, 1992, now abandoned, both of which are hereby incorporated by reference.

BACKGROUND OF THE INVENTION

The invention relates to a bioerodible device for administering active ingredients, said device being intended to be inserted into a body cavity. More particularly, it relates to a bioerodible device comprising a water-soluble mucoadherent lyophilized foam and an active ingredient; a method of using such devices; and a method for manufacturing such devices. The delivery device of the present invention adheres to mucosal tissue and is accordingly particularly suitable for use in administering active ingredients to both the buccal cavity and the vaginal cavity. The delivery device is used to provide for the controlled and sustained release of an active ingredient.

Prescription and over-the-counter medications and other pharmaceutical products have traditionally been administered through oral ingestion, nasal sprays, injection and suppositories. There are disadvantages associated with each of these methods of administration.

For example, with respect to oral ingestion of a drug, many patients, including pediatric and geriatric patients, frequently have great difficulty swallowing a pill. In addition, there is often a substantial delay between the time of oral administration of a drug until it has the desired therapeutic-effect in the patient's system. Generally, a drug must pass from the stomach into the small and large intestines before it will be absorbed into the patient's bloodstream. This typically takes about forty-five minutes or longer. Moreover, many drugs that are taken orally are metabolized almost immediately and thereby rendered ineffective by the patient's system before they can have the desired therapeutic effect.

Likewise, many patients also have at least some aversion to injections or suppositories. Moreover, neither of these methods are readily conducive to self-administration.

Consequently, many patients simply fail to comply with their physicians orders with respect to taking medications that are administered in these ways.

Compressed tablets or extruded thin films, including multi-layered products, that are inserted into the buccal cavity for delivering an active ingredient are known in the art. See, for example, U.S. Pat. No. 4,540,566, Davis et al. which discloses a compressed tablet comprising cellulose ether; U.S. Pat. No. 4,389,393, Schor et al., which describes a buccal delivery system consisting of a compressed tablet comprised of hydroxypropylmethylcellulose, or a mixture of methylcellulose and sodium carboxylmethylcellulose, and/ or other cellulose ethers; U.S. Pat. No. Re. 33,093, issued to Schiraldi et al.; U.S. Pat. No. 4,900,552, which discloses a trilaminate film comprised of a hydratable muco-adhesive base layer, a non-adhesive reservoir layer and a water-impermeable carrier film; U.S. Pat. No. 4,900,554, issued to Yanagibashi et al., wherein there is disclosed an adhesive device containing an adhesive layer and a water insoluble or sparingly soluble backing layer; and G.B. Patent No. 2,108, 841, which also discloses a multi-layered product comprising a non-adhesive layer and an adhesive layer.

However, although these devices are useful, there are also disadvantages associated with their use which renders them unsuitable for many applications and unacceptable to the patient. For example, many of these devices do not last very long. In U.S. Pat. Nos. 4,717,723 and 4,829,056, Sugden discloses a compressed tablet for dispensing prochlorperazine or etorphine (or a salt thereof), respectively. Sugden's devices are intended to remain in position and dispense a drug for up to 2 hours. Likewise, in European Patent Application No. 371,466, there is described a buccal tablet for administering estradiol that is designed to dissolve very rapidly (that is, in about one minute). Accordingly, these devices are not suitable when clinical indications require a longer release time.

Furthermore, the hardness of the devices makes them highly uncomfortable when placed in the buccal cavity. In addition, they are inconvenient to apply, bulky, and difficult to keep in place.

In the area of foams, although the use of foams and freeze-dried foams to deliver various active ingredients is well-known, such foams generally do not possess the requisite characteristics that would render them suitable for use as a muco-adherent delivery device. For example, in U.S. Pat. No. 4,642,903, Davies discloses the use of freeze-dried foams for dispensing a variety of active ingredients. However, Davies' foams are designed to have very rapid dissolution times (virtually instantaneous) which would render those foams highly ineffective for use as an active ingredient dispensing device when longer release times are required. Moreover, in Davies' foaming process it is not possible to control the degree of aeration which is critical in order to manufacture batches of devices having substantially equivalent properties. Accordingly, using Davies' method it is not possible to control the density, dosages, dosage delivery rate and dissolution time of the devices from manufactured batch to manufactured batch.

Similarly, in U.S. Pat. No. 4,292,972, Pawelchak et al. discloses a lyophilized foam sponge product containing sodium carboxylmethylcellulose, pectin, gelatin, and a pharmaceutical, that is intended primarily for use as a hemostatic agent. Unfortunately, Pawelchak's dispersions do not aerate readily; the freeze-dried foams tend to be brittle and dissolve too quickly.

Japanese patent Application No. 78-145170 describes a method for manufacturing a polyvinyl-alcohol-based sponge material intended for use as an operating sponge for hemostasis. The device is made by foaming aqueous polyvinyl alcohol solution having nonionic cellulose ethers dispersed therein, and freeze drying the foamed mixture at reduced pressure. The foams produced by this method have several disadvantages; they dissolve too rapidly, and upon lyophilization, the product is too stiff. Moreover, the method utilized to manufacture the devices suffers from the same disadvantages discussed above.

Accordingly, a need exists for a bioerodible mucoadherent delivery device that provides for the sustained and/or controlled release of an active ingredient which can be absorbed through the mucous membrane. Such a device should be convenient to insert, stay in place in the body cavity into which it is inserted, and be comfortable to wear in order to encourage the patient to self-administer the active ingredient.

Furthermore, there is a need for a method of producing such devices whereby the properties of the devices, including density, dissolution time, and active ingredient delivery rate, can be substantially controlled and readily reproduced.

SUMMARY OF THE INVENTION

It has been found that a device for insertion into a mucosa-lined body cavity comprising, a water-soluble muco-adherent lyophilized foam and an active ingredient, and having a density of about 0.001 to about 0.1 gm/cc and a dissolution time of at least about 8 hours, can provide for the sustained and/or controlled release of an active ingredient for at least 8 hours. Preferably, the device has a dissolution time of at least about 8 hours to about 24 hours, and therefore, is very slow to dissolve. In addition, upon dissolution, the device forms a viscous gels which maintains good structural integrity.

The muco-adherent delivery device of the present invention alleviates many of the problems recited heretofore. It can be easily inserted and manipulated by the patient. When used as a buccal delivery device, it has a very comfortable mouth feel so that the patient does not experience discomfort when using the device. It adheres readily to moist mucosal tissues; thus, it is easy to keep in place. Moreover, the device can provide for the sustained and/or controlled release of active ingredient into the body cavity for at least several hours. Accordingly, the device provides an ideal means for self-administration of an active ingredient.

In addition, the disadvantages associated with prior art methods of manufacture for active-ingredient-dispensing foams are overcome in the present invention. It has been determined that by using a continuous enclosed mixer (known as an Oakes foamer) to foam the dispersion, it is possible to regulate foaming parameters and thereby control the liquid density of the foamed dispersions prior to lyophilization. The inventors have found that by controlling the liquid density of the foamed dispersion, it is possible to achieve excellent control of the dissolution time, dosages, and other properties of the devices. The use of an enclosed foamer like the Oakes foamer for this purpose is heretofore unknown.

Accordingly, it is an object of this invention to provide a soluble device for delivery of an active ingredient which delivers an effective dosage of active ingredient across the mucous membrane for at least about 8 hours, and which has a dissolution time of at least about 8 hours.

It is another object of this invention to provide a soluble device for delivery of an active ingredient which can be easily inserted by the user, which is muco-adherent, which stays in position for a prolonged period, and which is completely and naturally soluble in the body cavity into which it is inserted, thereby obviating the need for removal.

It is a further object of this invention to provide a method for manufacturing the muco-adherent devices described herein, whereby the method provides for the production of devices having substantially equivalent densities, dissolution times, dosages, and softness and flexibility properties.

Further objects and advantages of the present invention will be made known in the following description of the preferred embodiments and claims.

DETAILED DESCRIPTION OF THE INVENTION

The device of this invention comprises a water-soluble muco-adherent lyophilized foam and an active ingredient, wherein the device has a density of about 0.001 to about 0.1 gm/cc and a dissolution time of at least about 8 hours. The devices provide for the sustained and/or controlled release of an active ingredient into a mucosa-lined body cavity for a prolonged period. The term "sustained release" means that the concentration of the active ingredient is maintained at a relatively constant level in the body cavity. The term "controlled release" means that the active ingredient is administered over a period of time.

As used herein, the term "muco-adherent device" means any solid substance, of any shape, which is intended to be inserted into a mucosa-lined body cavity and which will adhere to the mucosal tissue thereof. The term "buccal device" or "buccal delivery device" means a muco-adherent device which is intended to be inserted into the buccal cavity. The term "vaginal device" or vaginal delivery device" means a muco-adherent device which is intended to be inserted into the vagina.

Devices of the invention are intended to be inserted by the user and do not require fitting by a physician. They can be easily inserted digitally or with an applicator. Furthermore, they are completely and naturally soluble in the body cavity.

In use, the device is inserted into the pouch of the cheek or the vagina, and maintained in intimate contact with the mucosal tissue thereof for at least about 8 hours following in-vivo placement. Upon insertion and contact with the moist mucous membrane, the device naturally and slowly begins to dissolve by fluid absorption. As it dissolves, it continually releases an amount of active ingredient in active form into the body cavity area, at a rate which is sufficient to maintain a therapeutic or effective level of active ingredient. Preferably, the active ingredient is continually released for at least about 8 hours after insertion.

The device of the invention has good adhesion to the mucous membrane (i.e., the lining) of the body cavity. Upon contact with the mucus which is excreted by the mucous membrane, the muco-adherent device hydrates, thus adhering the device to the membrane. This feature permits the device to be worn comfortably and maintains it in proper position so that delivery of the active ingredient is not interrupted.

The active ingredient may be absorbed through the mucosal tissue, thereby avoiding undesirable hepatic first-pass metabolism and gastrointestinal incompatibility. However, it will be recognized that the active ingredient can also act locally in the body cavity. For example, as will be seen hereinafter, a vaginal delivery device can be used to administer an antifungal or other ingredient for local treatment of a vaginal infection such as a yeast infection or bacterial infection.

Upon dissolution, the lyophilized foam first forms a gel (i.e., a colloidal solution having the consistency of jelly), and then further dissolves into a liquid. The gel so formed possesses good structural integrity for a prolonged period prior to further dissolution to a liquid. For example, at least 2 hours after the devices of the invention have been placed in 1% saline solution at 37° C., a substantial amount of gel (at least about 10% by volume) still remains visible to the naked eye. This feature facilitates adhesion of the device, permits it to be used comfortably and helps to control the rate of delivery of the active ingredient.

The time required for the devices of the invention to attain substantially complete in-vitro dissolution to a liquid (i.e., no gel is evident), as measured by the method described below, is referred to as "dissolution time". By applying the teachings of this invention, dissolution times of at least about 8 hours can be obtained, preferably at least about 12 hours, even more preferably at least about 20 hours, and most preferably at least about 24 hours. Moreover, in-vivo dissolution times are likely to be even greater.

The procedure described in USP XXII, 711 DISSOLUTION, Apparatus 1, from U.S. Pharmacopeia, was followed to determine the dissolution time. This procedure uses an assembly consisting of a covered glass vessel (a Bell jar), a motor, a drive shaft, a basket, and a constant temperature-water bath. The speed regulating device used allows the shaft rotation to be selected and maintained at a rate of 35 rpm. The basket is affixed to the drive shaft. The vessel is filled with 400 ml of 1% (by weight) saline solution (pH 5-6). The device is placed into a dry basket at the beginning of each test, and the basket is immersed in the vessel containing the saline solution. The vessel is then immersed in a constant temperature water bath set at 37° C. The sample is observed, and as dissolution takes place, the time for total gelation is recorded. The test is allowed to continue and the time for total dissolution of the gel is also recorded.

The dissolution time, and other physical characteristics of the devices like density, flexibility and softness, are due to the selection of the particular water-soluble polymers and active ingredient, their respective amounts, and the novel manufacturing process described herein.

The first step in producing the lyophilized foam devices of the invention comprises forming an aqueous dispersion comprising at least one, and preferably several, water-soluble polymers, and an active ingredient. The term "aqueous dispersion" as used herein is meant to include dispersions (including solutions) in which the solvent is water and optionally, water-miscible liquids.

Preferably, the polymer and the active ingredient are added to the solvent and dispersed. Alternatively, the polymer is initially added to the solvent and dispersed, followed by addition and dispersion of the active ingredient. If necessary, heat can be applied to the mixture to facilitate dispersion.

Typically, polymer is added to the dispersion at a concentration of about 0.1% to 20% (by weight of the total dispersion including active ingredient), preferably about 1% to about 15%, even more preferably about 2% to about 10%. At lower concentrations, there may be insufficient polymer to prepare a sturdy foam, whereas at higher concentrations, the dispersion may be too viscous to foam under normal conditions.

Cellulose, cellulose ethers and derivatives thereof, and polymers of the type disclosed in U.S. Pat. No. 4,615,697, issued to Robinson, and commercially available under the generic name "polycarbophil" are suitable for use in the present invention.

Other suitable polymers include polycarboxylated vinyl polymers, including polyacrylic acid polymers, polyacrylic acid polymers that are lightly crosslinked with a polyalkenyl polyether (such as those commercially available from B. F. Goodrich, Cincinnati, Ohio, under the trademarks Carbopol® 434, 934P, 940 and 941), polysaccharide gums (such as natural plant exudates including e.g., karaya gum, ghatti gum and the like), and seed gums (including e.g., guar gum, locust bean gum, psigllium seed gum and the like). Cross-linked alginate gum gels of the type described in U.S. Pat. No. 3,640,741, to Etes are also suitable.

Preferably, the polymer is selected from the group consisting of polyurethanes, gelatins, celluloses and cellulose ethers, including hydroxypropylmethylcellulose, sodium carboxylmethylcellulose, methylcellulose, hydroxethlcellulose, hydroxypropylcellulose, hydroxyethylmethylcellulose, hydroxyethylethylcellulose, hydroxypropylethylcellulose, CARBOPOL®, polyvinyl alcohol and derivatives thereof, dextran, chitosan and its derivatives, starch and its derivatives, polyacrylamides, polyacrylates, agar, collagen, fibronectin, alginic acid, pectin, hyaluronic acid, or mixtures thereof.

Foams comprised of cellulose ethers are especially preferred. In particular, it has been found that devices comprising hydroxypropylmethylcellulose (HPMC), sodium carboxylmethylcellulose (CMC), or mixtures thereof, possess excellent qualities, including good adhesive properties. Devices comprised of foams made from a HPMC, or mixtures of HPMC and CMC, when placed in the buccal cavity of two male volunteers, remained in intimate contact with the mucosa about two hours after insertion.

Certain polymers, such as cellulose ethers generally and hydroxypropylmethylcellulose in particular, may be employed to provide liquid foams having good stability and structural integrity, and dry foams with desirable softness. Other polymers, like gelatin, may be incorporated in the devices of the invention to make them sufficiently rigid, so that the device can be inserted without breaking or fracturing. One skilled in the art can readily determine the polymeric ingredients and their amounts that result in a device having the preferred combination of suitable properties.

It has been found that when a mixture of hydroxypropylmethylcellulose and sodium carboxylmethylcellulose is used, the polymers preferably are combined in an initial ratio of about 4:1 to about 1:1 (by weight of the dry solids), in order to produce a sturdy, but soft and flexible dry foam. Ratios of about 3:1 to about 2:1 are even more preferred.

Various active ingredients may be incorporated into the devices, including for example, pharmaceuticals, nutrients and diagnostics, but active ingredients comprising pharmaceuticals are preferred. The active ingredient may be selected from the group of analgesics, anorexics, antiarthritics, antibacterials, antibiotics, anticonvulsants, anti-depressants, antidiabetics, anti-fungal agents, antihistamines, anti-hypertensives, anti-inflammatories, anti-microbials, anti-neoplastics, anesthetics, anti-virals, cardiovascular, vasodilators, vasoconstrictors, decongestants, diuretics, hormones, muscle relaxants, tranquilizers, polypeptides, vitamins and the like.

Hormones and peptides are especially preferred. In an especially preferred embodiment of the device, the active ingredient comprises histrelin or estradiol.

The active ingredient may be provided in the dispersion at a concentration of about 0.005% to about 25% (by weight of the total dispersion), with about 0.01% to about 10% being preferred. The active ingredient may be present at from abut 0.005% to abut 95% by weight of the (dry) device, with about 0.1% to about 80% by weight being preferred. Drug therapeutic value dictates the required concentration of active ingredient.

The amount of active ingredient incorporated into the device affects its therapeutic efficacy, its tactile and structural properties, and the ease with which it may be manufactured. For example, devices containing relatively high percentages of active ingredient may result in an increase in the level of active ingredient available for absorption through the mucosal tissue. However, if the active ingredient is too high, such devices may have an inadequate dissolution time and an unpleasant feel. Devices having lower percentages of liquid active ingredient may be too brittle; however, they may possess more desirable dissolution times. If the active ingredient is a solid, such devices may be too brittle to be conveniently inserted. Accordingly, it is necessary to empirically determine the amount of active ingredient that results in a device having the preferred combination of suitable properties.

The devices of the invention may contain additional materials including, but not limited to, preservatives, fillers, excipients, binders, plasticizers, surfactants, wetting agents or penetration agents.

All materials incorporated into the devices should be blended into a homogeneous mixture (in the aqueous dispersion) prior to foaming.

In order to ensure that the aqueous dispersion will subsequently foam, the viscosity of the dispersion should be maintained at about 3000 to 7000 cps, preferably about 3500 to 6000 cps, most preferably about 4000 to 5000 cps, as measured by a Brookfield viscometer at ambient temperature using a number 4 spindle at 20 rpm. Accordingly, it may be necessary to cool the dispersion, preferably to about 32° to 35° C., with mixing in order to maintain its viscosity.

After all materials to be incorporated into the device have been blended into an aqueous dispersion having adequate viscosity for foaming, the dispersion is transferred to a continuous, enclosed mixer known as an "Oakes" foamer. An Oakes foamer is capable of operating under pressure to foam the dispersion, and typically is used to manufacture creamy, smooth food products like ice cream and marshmallows. U.S. Pat. Nos. 2,572,049, 2,600,569, 2,679,866, and 3,081,069 describe various Oakes foamers useful for practicing the method of the invention, and the disclosures of these patents are incorporated herein by reference. The model referred to as the Oakes 2" Mixer, Model No. # 2MT.5A is especially preferred for use in practicing the invention.

An Oakes foamer is comprised of an electrical system, an air system and a product section. Generally, it comprises a pump; a mixing chamber; a head assembly having a rotor; a gas inlet; an outlet for the foamed dispersion; means to measure pump speed and rotor speed, flow rate, and pressure of an incoming gas; and means to measure the back pressure of the foamed dispersion.

The electrical system consists of a main power switch, and two independently variable speed controllers and motors with digital tachometers to measure the rotor and pump speed.

The air system consists of a manual on/off toggle valve, pressure regulator and gauge, an adjustable flow valve and meter and a one way (check) valve.

The product section consists of a positive displacement pump; speed reducer; inlet piping; a back pressure gauge to monitor back pressure; and a mixing chamber. The back pressure gauge is isolated from the product by a diaphragm seal assembly.

A liquid dispersion is fed to the pump, transmitted through a line to the mixing chamber wherein it is combined with air under pressure, and mixed by the head assembly with the rotor. In the mixing chamber, the dispersion is foamed and the air and the dispersion are blended into a substantially uniform, homogeneous mixture. From the mixing chamber, the foamed dispersion is then sent to an outlet pipe.

It has been determined that the operating parameters of the mixer are primarily responsible for determining the density of the liquid foam, and consequently, the properties of the devices produced. For example, increasing the pressure and/or flow rate of air into a fixed volume of dispersion generally produces a more flexible, faster dissolving device. Similarly, changing the pump speed and/or the rotor speed, also changes the liquid density of the foamed liquid dispersion. The use of an enclosed foamer (like an Oakes foamer) permits each of these process variables to be separately monitored and independently altered in a controlled manner.

Thus, it is possible to empirically determine the settings of the foamer which will produce a foamed dispersion having a desirable liquid density and, upon subsequent lyophilization, bioerodible, muco-adherent devices having suitable qualities. Moreover, the use of such a foamer makes it possible to accurately reproduce the settings so that a batch of devices having substantially identical properties and dosages is manufactured in each manufacturing sequence.

It has also been found that the devices of the invention (when they are made by lyophilizing an aqueous solution or dispersion of a water soluble polymer and an active material wherein the aqueous solution or dispersion has been foamed prior to lyophilization) should have a (dry) density of about 0.001 to about 0.15 gm/cc, preferably about 0.001 to about 0.08 gm/cc, more preferably about 0.01 to about 0.08 gm/cc, as determined using techniques which are well-known to those of ordinary skill in the art. A device having a density within these ranges possesses a good dissolution time. In addition, such devices are sufficiently sturdy, yet soft and flexible, so that the devices are comfortable to the user and yet do not readily break upon insertion.

When devices of the invention are made by lyophilizing a substantially gas-free, i.e. unfoamed, solution or dispersion of a water soluble polymer and an active material, the dry density of the device should range from about 0.06 g/cc to about 0.30 g/cc, preferably, from about 0.10 g/cc to about 0.16 g/cc.

Typically, in order to achieve devices with good physical characteristics, good dissolution times, and which are sufficiently efficacious at prolonged periods, foamer conditions are set as follows; pump speed about 25–30rpm, air flow rate about 100–220 cc/min (at 100 psig input pressure), and rotor speed about 1000–2300 rpm. The foam that results generates a back pressure of 10–40 psig during extrusion. Of course, the conditions are approximate since operational variability occurs in the meters during operation of the foamer. In addition, the dispersion probably has some air in it due to the dispersion formulation step. Prior degassing will likely alter the density of the solution and require a change in the liquid/air ratio in the foamer.

Any of these process variables can be changed, thereby changing the liquid density of the foam. In order to determine how the liquid density of the foam as well as the device produced from that foam are affected, foams are manufactured using the Oakes foamer wherein one process variable is varied while all other parameters remain constant.

For example, a series of foams of varying liquid density can be produced by varying the flow rate of the incoming gas. The liquid density of the resulting foam is determined using techniques that are well-known in the art. A curve is subsequently generated by plotting the density of the foamed liquid dispersion versus the flow rate.

The foamed dispersion from each run is then lyophilized (that is, freeze-dried under vacuum). Upon lyophilization, the device (whose foamed liquid density is known) is evaluated to determine whether it has certain characteristics, including an adequate dissolution time. In this manner it is possible to determine the liquid density which, upon lyophilization, results in a device having a combination of suitable properties. Thus, the settings necessary to foam the dispersion to the desired liquid density can be readily determined empirically or from the graph, and more importantly, controlled by the operator of the foamer who can easily reset the gas flow rate or any other process variable on the foamer to the appropriate setting to achieve reproducible results.

Therefore, by using the method of the invention one can substantially control the liquid density of the foamed dispersions, and ultimately, the properties including dosage, dosage delivery rates and dissolution times of the devices so produced.

Foaming can be continued until the back pressure gauge reaches an equilibrium value. Alternatively, one skilled in the art can readily determine when sufficient foaming has occurred by inspecting the viscosity of the foamed dispersion as it is extruded. Preferably, the density of the liquid foamed dispersion should range from about 0.1 to about 1.0 gm/cc. Liquid foam densities of about 0.4–0.6 gm/cc are even more preferred.

In the next step, the foamed liquid dispersion is placed into a receptacle having a known volume ("unit dosage"). Since the liquid density of the foam and the volume of the receptacle are known, it is a simple calculation to determine the foam weight and the amount of active ingredient incorporated into each unit dosage.

Accordingly, one skilled in the art can readily manufacture batches of devices containing known and substantially equivalent dosages of active ingredient.

Although the foam can be cast into sheet form, it is preferably extruded through tygon tubing into a pre-formed mold. Various aluminum, plastic and release liner covered molds can be employed. Release-coated aluminum molds are preferred, since the devices easily release from these molds without cohesive failure.

It is also preferred to extrude the foam into compartmentalized trays whereby the volume of one compartmental unit equals the volume of the resulting device. This prevents uncontrolled spread or flow of the foam and thus, the manufacture of devices which have nonuniform dimensions and dosages.

The foamed dispersion is then lyophilized in a freeze drier in order to generate an open cell foam device which contains the active ingredient. A Virtis 800L-Freezemobile 12 is preferred. The freeze-drier shelves are chilled to below about −40° C. The condenser is chilled to below about −50° C. The filled molds are placed on the shelves and frozen to shelf temperature. The frozen foam is then exposed to the full vacuum (10–90 millitorrs) of the unit. Once this vacuum is achieved, the shelf temperature is gradually increased to about room temperature and sublimation continues, preferably for at least about 15 hours, or until the sample temperature reaches about 20°–25° C.

Thermal gravimetric analysis may be used to determine the water content of the foams. It may also be used to determine the thermal stability of the devices by determining degradative weight loss.

Typically, residual water is present at about 5% by weight of the final dried product.

The active ingredient content of the devices may be determined using ultraviolet, HPLC, or any other known analysis of a solution of the dissolved foam, or analysis of the dried bioerodible device.

The invention is further illustrated by the following examples which are not intended to be limiting.

EXAMPLES

Example 1—Preparation of a Histrelin Containing Buccal Delivery Device

STEP 1. Dispersion Preparation

Deionized water (330 g) was heated to 190° F. To this 20 g of hydroxypropylmethylcellulose (Methocel E4M-Dow Chemical, Midland, Mich.) was added with stirring. After 5 minutes, 650 g of deionized water cooled to 20° C. was added with stirring. The hydroxypropylmethylcellulose was dissolved after the solution had degassed, 750 g was mixed with 1.8 g of histrelin. The mixture was stirred until the histrelin was dissolved.

STEP 2. Foaming Procedure

The solution of step 1 was added to the hopper of an Oakes Foamer (Model 2MT. 5A). The solution was pumped through the system at a speed of about 25 rpm until equilibrium was attained. The initial 100–150 ml was purged and discarded. The remainder was recirculated. The rotor of the mixing head assembly was set at 1650 rpm and turned on. The air pressure was set at 100 psig and a flow rate of 220 cc/min. The foam was generated at a back pressure of 40 psig and had a measured liquid density of 0.52 gm/cc. The foam was extruded through ¼" tygon tubing and collected as a cast sheet in a tray having dimensions of 23×33×0.5 cm. The top of the tray was scraped to eliminate excess foam and to produce a smooth, even surface.

STEP 3. Lyophilization Procedure

The liquid foam sample was then placed on the shelf of a Virtis freeze drier (Unitop 800 L with Freezemobile 12). These shelve were pre-chilled to −45° C. The frozen foam was lyophilized at full vacuum (20–60 millitorr) to a terminal temperature of 20° C. The drying time was about 16 hours.

In-Vitro Foam Dissolution Studies

The U.S.P. procedure described heretofore was followed to determine the dissolution times for the devices produced. The devices (400 mg samples) were placed in baskets and immersed in 400 ml of 1% saline solution, in a water bath set at 37° C. The dissolution times were recorded upon visual inspection.

In-Vivo Delivery Study of the Histrelin Containing Buccal Delivery Device

The study was designed to measure the ability of the histrelin delivered by the soluble buccal devices of the invention to induce ovulation in the diestrus rat. Devices were prepared by punching 7 mm tablets from the tray containing the lyophilized foam. Each tablet theoretically contained 297 ug of histrelin. Whole, halved and quartered tablets were then placed in the buccal cavity of diestrus rats anesthetized with ether. After 10 minutes the device was absorbed. The following day the rats were sacrificed and the oviducts removed and examined for the presence of ova.

As shown in Table I below, the tablets were effective in inducing ovulation in a dose-dependent manner with a ED50 dose of approximately 75 ug/rat or 300 ug/Kg.

TABLE I

| Buccal Tablet | Histrelin,*ug | Ova/Rat | # of Rats Ovulating /Total # of Rats |
|---|---|---|---|
| Whole | 300 | 13 | 6/6 |
| Half | 150 | 8 | 4/5 |
| Quarter | 75 | 6 | 4/6 |

*micrograms

Example 2—Preparation of an Estradiol Containing Buccal Delivery Device

STEP 1. Dispersion Preparation

A solution containing 2% HPMC was prepared as in Example 1. About 0.2 g of estradiol was added with stirring to about 3000 g of a 2% hydroxypropylmethylcellulose solution at 25° C. The solution was stirred for several minutes until all particles were dispersed.

STEP 2. Foaming Procedure

The solution of step 1 was added to the hopper of an Oakes Foamer (Model 2MT. 5A). The solution was pumped through the system at a speed of about 55 rpm until equilibrium was attained. The initial 100–150 ml was purged and discarded. The remainder was recirculated. The rotor of the mixing head assembly was set at 2150 rpm and turned on. The air pressure was set at 100 psig and a flow rate of 340 cc/min. The foam was generated until a back pressure equilibrium was attained, at which point it had a measured liquid density of 0.46 gm/cc. The foam was extruded through ⅜" tygon tubing and cast into a tray of the dimensions 46.5×25.6×0.8 cm. The (average) weight of the liquid foam in the tray was 385 g. The liquid flow rate was 479 g/min. The anticipated dosage was 10 ug/7 mm diameter unit.

STEP 3. Lyophilization Procedure

The same procedure described in Example 1 was repeated.

In-Vivo Delivery Study of the Estradiol Containing Buccal Delivery Device

The devices prepared in Example 2 were evaluated in ovariectomized Sprague-Dawley rats. The rats were ovariectomized 2 weeks prior to testing. On the test day the animals were anesthetized with ether and administered with either 10 ug of 17 B-estradiol in sesame oil [0.2 ml by subcutaneous (S.C.) or ingestion (I.G.) routes] or a soluble device containing an equal amount of estradiol placed buccally. Animals were kept anesthetized for approximately 10 minutes after estradiol administration. Trunk blood was collected at various times thereafter. Serum 17 B-estradiol levels were then measured in a single radioimmunoassay and are reported in Table II.

TABLE II

SERUM ESTRADIOL LEVELS AFTER ADMINISTRATION OF 10 ug OF 17 B-ESTRADIOL BY VARIOUS ROUTES TO OVARIECTOMIZED RATS

| | Hours After Treatment | | | |
|---|---|---|---|---|
| | 0.5 | 1.0 | 2.0 | 4.0 |
| Vehicle (Sesame Oil) | 8.3 +/ −3.8* | | | |
| S.C. | 1845 +/− 137 | 1539 +/− 264 | 1286 +/− 150 | 607 +/− 195 |
| I.G. | 24 +/− 6 | 18 +/− 3 | 29 +/− 6 | 27 +/− 6.0 |
| Buccal | 258 +/− 38 | 221 +/− 63 | 80 +/− 26 | 35 +/− 6 |

*picograms per milliliter

As indicated by the results set forth above, the bioavailability of estradiol administered buccally was greater than oral administration but less than administered by injection. However, the observed 3 to 5 fold increase in the level of bioavailable drug administered by the buccal device versus oral administration in the first 1 to 2 hours was significant.

Example 3

Using the manufacturing methods described herein, it is possible to produce foams having (in-vitro) dissolution rates of at least about 7.5 hours to at least about 23 hours. Table III presents data on the dissolution times achieved by foams representative of those used in the invention (Examples 4–15) and comparative examples (Examples 1–3).

TABLE III

| Sample | Dissolution Time, hours |
|---|---|
| 1. (6% PVA solution)* | 7.5 |
| 2. (6% PVA foam)* | 4 |
| 3. (3:1:1 gelatin/pectin/CMC)** | 4.75 |
| 4. (2% HPMC Solution) | 23 minimum |
| 5. (2% HPMC, 100 cc/min air) | 23 minimum |
| 6. (2% HPMC, 200 cc/min air) | Between 7.5 and 20.5 h |
| 7. (2% HPMC, 300 cc/min air) | Between 7.5 and 20.5 h |
| 8. (67/33 HPMC/CMC HP-12HS) | 20 minimum |
| 9. (75/25 HPMC/CMC HP-12HS) | 20 minimum |
| 10. (67/33 HPMC/CMC HP-5HS, lower MW) | 20 minimum |
| 11. (75/25 HPMC/CMC HP-5HS) | 20 minimum |
| 12. (67/33 HPMC/HP-SB, lower MW) | 7.5 |
| 13. (75/25 HPMC/HP-SB, lower MW) | 7.5 |
| 14. (67/33 HPMC/HP-SH, lower NW) | 22 |
| 15. (75/25 HPMC/HP-SH, lower MW) | 22 |

*The percentage indicates the percentage of polymer added to the liquid dispersion by weight (prior to foaming).
**The ratio indicates the initial ratio of polymers added to the aqueous dispersion.

In comparative Examples 1 and 2, the control solution and the foam was comprised of polyvinylalcohol (Airvol 540, Air Products, Allentown, Pa. ) and was prepared in accordance with the teachings of Japanese Patent Application No. 78-145170. The foam of Example 3 was prepared in accordance with the description set forth in U.S. Pat. No. 4,292, 972, Example 3.

Examples 4–15 were comprised of foams containing hydroxypropylmethylcellulose (Methocel E4M, obtained from the Dow Chemical Company, Midland, Mich. ). Examples 8–15 were further comprised of sodium carboxymethylcellulose of various molecular weights including Cellogen HP-12HS, having a molecular weight of 330,000 to 380,000, Cellogen HP-5HS, having a molecular weight of 290,000 to 315,000, Cellogen HP-SB, having a molecular weight of 75,000 to 83,000, and Cellogen HP-SH, having a molecular weight of 146,000 to 153,000 (each of which are available from Montello, Tulsa, Okla. ). The preferred carboxymethylcellulose was Cellogen HP-12HS.

As the data above shows, the foams of the prior art dissolved in 4 to 7.7 hours. The Sample 3 foam exhibited poor structural integrity. The foam produced in accordance with the teachings of the Japanese Patent Application was too stiff.

On the other hand, the foams of the invention were soft and pliable, exhibited good structural integrity over time, and had good bioadhesion. Moreover, as indicated above, they had dissolution times of about 7.5 hours to over 23 hours. Accordingly, the foams are superior to those prepared in accordance with the prior art.

As indicated earlier herein, various active ingredients can be incorporated into the devices of the present invention for subsequent delivery of that active ingredient. For example, an antifungal drug may be incorporated into devices of the present invention and the resulting devices used as a vaginal suppository. In use, the device is inserted into the vagina after which the antifungal ingredient is released so as to function, for example, as a treatment for vaginal yeast infections.

The following Examples show the preparation of water soluble, muco-adherent vaginal delivery devices containing miconazole nitrate and terconazole, both of which are antifungal drugs.

Example 16

A water-soluble, muco-adherent drug delivery device comprising miconazole nitrate (MN) was prepared as follows. An aqueous dispersion of miconazole nitrate and hydroxpropylmethyl cellulose (HPMC) was first prepared. 5174 grams of sterile water were added to a 3-gallon stainless steel container fitted with an electric mixer and heated to 180° F. A dry blend of 406 grams of miconazole nitrate and 420 grams of HPMC was gradually added to the heated water with agitation over the course of five (5) minutes. Stirring was continued for a period of five (5) minutes after completion of the addition of the dry blended materials. The resulting dispersion was cooled to room temperature over a period of thirty (30) minutes with continued stirring. The cooled dispersion had a milky coloration, a density of 1.04 g/cc., and a Brookfield viscosity of about 5350 centipoises (cps) when measured using a No. 4 spindle at 10 rpm and 78° F. (25.6° C.). The dispersion consisted of 7.0% by weight of HPMC, 6.8% by weight of miconazole nitrate and 86.2% by weight of water. The dispersion was substantially free of any entrained air. The HPMC was obtained from Dow Chemical Company under the designation Methocel* E50-LV Premium. According to the supplier, Methocel, E50-LV Premium has the following characteristics:

a methoxyl content of 28–30% (ASTM Test Method D3876);

a hydroxypropyl content of 7.0–12.0% (ASTM Test Method D3876); and a viscosity (2% in water @20° C.) of 40–60 cps (ASTM Test Method D2363).

The above described HPMC/MN aqueous dispersion was charged to the hopper of the Oakes foamer machine mentioned in Example 1. The Oakes foamer was used to pump the dispersion into a released-coated aluminum split mold having 120 bullet-shaped mold cavities each having a maximum diameter of about 1 cm and a depth of about 3 cm. The Oakes machine was operated without the introduction into the aqueous dispersion of any compressed gas, i.e., the dispersion delivered to the split mold was not aerated or foamed.

The dispersion filled split mold was then placed on a shelf of the VIRTIS freeze drier mentioned in Example 1. The chamber of the freeze drier had been pre-chilled to –44° C. (condenser temperature was –64° C.) The foam was allowed to freeze over a period of about two (2) hours. The frozen foam was then lyophilized (i.e. freeze-dried) at full vacuum (20–60 millitor) to a terminal temperature of 20° C. The lyophilization time was about fifteen (15) hours. The freeze-dried, cylindrical shaped, foam devices were released from the mold cavities and stored in air-tight containers to await further testing. The resulting foam devices, suitable for use as vaginal suppositories, had an average weight of 0.288 grams, were chalky white in color had a maximum diameter of 0.9 cm, a length of about 2.8 cm and a density of about 0.144 gm/cc.

Six (6) of the foam devices were tested for In-Vitro Foam Dissolution Times in the manner described in Example 1 except that the shaft rotation was set at 30 RPM and the baskets containing the test samples were immersed in 900 mls. of a citric acid/disodium hydrogen phosphate heptahydrate buffer with an ionic strength of 0.1M KCl and pH of 4.0. A pH of 4.0 was chosen because it is the pH at which miconazole nitrate most readily dissolves and because it is in the middle of the pH range, i.e. 3 to 5, of the normal healthy vagina.

The Dissolution Time, average of six determinations, was about six (6) hours. Control samples, i.e. the same device without miconazole nitrate, had an average weight of about 150 mgs., an average Dissolution Time of about 6 hrs and a density of about 0.075 gm/cc. The aqueous dispersion foam from which the controls were prepared consisted of 7.5% HPMC and 92.5% water.

Example 17

A water-soluble, muco-adherent drug delivery device comprising terconazole, another anti-fungal ingredient, was prepared as follows. An aqueous dispersion of terconazole and hydroxypropylmethylcellulose was first prepared. 2634 gram of sterile water and 30 grams of benzyl alcohol were added to a 4 liter glass beaker were fitted with an electric mixer and heated to 180° F. A dry blend of 120 gm of terconazole (TER) and 216 gms of HPMC was gradually added to the heated water with agitation over the course of five (5) minutes. Stirring was continued for a period of thirty (30) minutes after completion of the addition of the dry blended materials. The resulting dispersion was cooled to room temperature over a period of forty (40) minutes while stirring was continued. The cooled dispersion had a murky coloration, a density of 1.04 gm/cc, and Brookfield viscosity of about 5100 centipoises (cps) when measured using a No. 4 spindle at 10 rpm and 78° F. The dispersion consisted of 7.2% by weight of HPMC, 4.0% by weight of terconazole, 1.0% by weight benzyl alcohol and 87.8% by weight of water. The dispersion was substantially free of any entrained air. The HPMC used in this Example 17 was obtained from Dow Chemical Company under the designation Methocel* E50-LV Premium. The above-described aqueous dispersion containing HPMC, terconazole and benzyl alcohol was charged to the hopper of the Oakes foamer machine mentioned in Example 1. The Oakes foamer was used to pump the dispersion into the same release coated aluminum split mold mentioned in Example 16. As was the case in Example 16, the Oakes machine was operated without the introduction into the aqueous dispersion of any compressed gas, i.e., the dispersion delivered to the split mold was not aerated or foamed.

The dispersion filled split mold was then placed into the freeze drier and subsequently freeze dried and lyophilized in the same manner as set forth in Example 16. Whereas the lyophilization time in Example 16 was about 15 hours, the lyophilization time in this Example 17 was about 17 and ½ hours.

The resulting foam devices, also suitable for use as vaginal suppositories, had an average weight of 0.244 grams, were chalky white in color, had a maximum diameter of about 0.9 cm, and a length of about 2.8 cm. The density of the devices was about 0.122 gm/cc.

Six of the foam devices of this Example 17 were tested for their In Vitro foam Dissolution Times in the manner described in Example 16. The dissolution time of the Example 17 devices, average of 6 determinations, was about six (6) hours. Control samples, identical in composition to those referred to in Example 16, also had an average dissolution time of about 6 hours. The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. An improved method for manufacturing a buccal delivery device for orally administering an active ingredient comprised of water-soluble lyophilized foam and an active ingredient, said method comprising the steps of:

(a) forming an aqueous dispersion comprising at least one water-soluble polymer and at least one active ingredient;

(b) providing a continuous, enclosed mixer capable of operating under pressure to foam the dispersion, said continuous mixer comprising a pump, a mixing chamber, a mixer assembly having a rotor, a gas inlet, an outlet for foamed dispersion, means to measure a rotor speed, a pump speed, a flow rate and pressure of an incoming gas, and mean to measure a back pressure of the foamed dispersion;

(c) selecting a target density for the foamed liquid dispersion, and a target dosage of active ingredient for the device;

(d) setting a pump speed;

(e) setting a rotor speed;

(f) setting a pressure and flow rate for an incoming gas;

(g) increasing the viscosity of said dispersion of step (a) until it has a viscosity sufficient to foam;

(h) transferring said dispersion to said mixer, and then foaming said dispersion until the density of the dispersion is substantially equal to the target density;

(i) measuring the back pressure of the foamed dispersion;

(j) placing said foamed dispersion into a receptacle of known volume; and (k) lyophilizing said dispersion to produce a lyophilized foam;

whereby the dosage of active ingredient in the lyophilized foam is substantially equal to the target dosage.

2. The method of claim 1 wherein the liquid density of the foamed dispersion of step (h) is from about 0.1 to about 1.0 gm/cc.

3. The method of claim 1 wherein the liquid density of the foamed dispersion of step (h) is about 0.5 gm/cc.

4. The method of claim 1 wherein step (a) comprises providing a dispersion comprising hydroxypropylmethylcellulose and sodium carboxylmethylcellulose in a ratio of about 4:1 to about 1:1 by weight.

5. The method of claim 1 wherein step (a) comprises providing polymer in the dispersion at about 0.1% to about 20% by weight.

6. The method of claim 1 wherein step (a) comprises providing polymer in the dispersion at about 1% to about 15% by weight.

7. The method of claim 1 wherein step (a) comprises providing polymer in the dispersion at about 2% to about 10% by weight.

8. The method of claim 1 wherein step (j) comprises extruding said dispersion into a compartmentalized tray comprised of identical units of known volume, whereby the dosage of active ingredient in each unit is substantially equal to the target dosage.

9. The method of claim 1 wherein the foamed dispersion is lyophilized in a freeze-drier-at full vacuum for at least 15 hours.

* * * * *